United States Patent [19]

Gold

[11] Patent Number: 4,871,358
[45] Date of Patent: Oct. 3, 1989

[54] EXTERNALLY-BASED INVERSIONARY TUBE

[76] Inventor: Steven K. Gold, 2611 Woodberry Rd., Broomall, Pa. 19008

[21] Appl. No.: 117,947

[22] Filed: Nov. 9, 1987

[51] Int. Cl.⁴ ............................................. A61M 5/00
[52] U.S. Cl. ................................... 604/271; 604/165
[58] Field of Search .............................. 604/271, 165; 254/134.4

[56] References Cited

U.S. PATENT DOCUMENTS

| | | | |
|---|---|---|---|
| 3,332,424 | 7/1967 | Minteer | 604/271 |
| 3,515,137 | 6/1970 | Santomieri | 604/165 |
| 3,766,916 | 10/1973 | Moorehead et al. | 604/165 |
| 3,866,601 | 2/1975 | Russell | 604/271 |
| 3,911,927 | 10/1975 | Rich et al. | 604/271 |
| 4,526,175 | 7/1985 | Chin et al. | 604/271 |
| 4,613,329 | 9/1986 | Bodicky | 604/165 |
| 4,615,331 | 10/1986 | Kramann | 604/271 |
| 4,642,101 | 2/1987 | Krolikowski et al. | 604/164 |
| 4,723,942 | 2/1988 | Scott | 604/164 |
| 4,728,322 | 3/1988 | Walker et al. | 604/164 |

FOREIGN PATENT DOCUMENTS

2406823  8/1975  Fed. Rep. of Germany ...... 604/271

*Primary Examiner*—Dalton L. Truluck
*Assistant Examiner*—Denise Whelton

[57] ABSTRACT

This invention provides a medical catheter designed to allow the outer surface of the tube which is adjacent to body tissue to remain stationary relative to such tissue during advancement and retraction of the catheter. This provides many advantages over conventional type catheters, including improved sterility, greater bacterial and debris control, less tissue trauma, reduced pain for the patient, and cost efficiency, both in terms of low initial expense, and minimized expense directly related to a subsequent reduction in catheter-related complications.

9 Claims, 6 Drawing Sheets

EXTERNALLY-BASED INVERSIONARY TUBE

BACKGROUND OF THE INVENTION

The term "catheter" is applied to any tubular instrument which is inserted into a body cavity, either naturally or surgically created, for the purpose of transporting solids, liquids and gases to or from such cavity in a controlled manner within the channel described by the tube. Catheters, capable of transporting oxygen, blood, body wastes, drugs, nutrients and other matter, are indispensible to the medical field and the art of saving lives.

The concept of the medical catheter has existed for over five thousand years. Original catheters were crudely constructed tubes made of metal Such instruments were discovered amidst the ruins of Pompeii, which was buried in the year 79 A.D. An interesting account of this early use of the medical catheter may be found in an article by Roy A. Tucker, entitiled "History and Sizing of Genitourinary Instruments," in the September 1982 issue of *Urology* (pages 342–349).

The origination of the modern catheter is attributed to Lorenz Heister, who developed an instrument shaped to fit the prostatic urethera in the early 1700's. Benjamin Franklin was one of the first to improve upon this idea, creating a uretheral catheter for use by a family member suffering from prostatic obstruction.

To date, the most significant development in this field has been the Foley catheter, invented by Dr. Frederick Foley around 1945. This type of catheter, would continues to be popular in the urological market despite its many problems, is inserted into the uretheral tube with the ocassional aid of a stylet: a thin metal rod placed within the catheter tube which provides some rigidity to the tube to facilitate insertion. The Foley catheter also includes a balloon at its distal end which is inflated once within the bladder to secure the tube in its desired position.

Other catheters, although not as well known as the Foley catheter, provide certain advantages for specific applications. Some of these catheters are improvements upon the Foley catheter while others provide completely innovative solutions to specific application problems.

Schiff U.S. Pat. No. 4,467,790 discloses an intra-aortic catheter which posesses a balloon which is capable of being elongated and therefore reduced in its diameter so that it may fit through a small diameter percutaneous sheath inserted into an artery.

Fuqua U.S. Pat. No. 4,601,713 discloses a variable diameter catheter which may be folded longitudinally to facilitate insertion, reducing the risk of infection and minimizing trauma.

Lin U.S. Pat. No. 4,211,233 discloses a balloon catheter with provisions to facilitate insertion and removal by means of releasing lubricants from openings in the side of the catheter.

Taylor U.S. Pat. No. 4,259,960 discloses an arrangement which is intended to prevent the balloon segment of a catheter from adhering to the shaft of a catheter.

Chin and Fogarty U.S. Pat. No. 4,493,711 discloses a cartheter posessing a partially-folded section at its distal end, which is activated by means of pressurized non-compressible fluid.

This last reference is one of two prior art patents believed to have any relevance to the present disclosure. This is due to the characteristic action at the distal end of that tube. However, the tip of that catheter is an "inverted-evertable non-elastic" section which is a piece separable from the tube, made of a material different from the material of the tube, and of "a diameter throughout equal to or greater than the catheter body." Furthermore, that catheter assembly requires multiple folds at the end of the "inverted-evertable" section to seal the tip during its extension to a predetermined length. This "multi-fold" configuration proves detrimental to the intended purpose of the tube due to the abrasion which occurs as the folded sections unfold. Subsequently, that catheter must be forcibly moved into and out of the body in the same manner as any conventional catheter, with its walls moving abrasively relative to the body tissue it comes into contact with. Also, that catheter posesses no provisions for retraction of the evertable section, does not allow for fine control of the length of the everted section, does not provide for precise control of the speed of extension, does not indicate to the physician the exact position of the distal end and requires a valve and piston arrangement and a non-compressible "pressurized fluid" for deployment of the inverted section, which remains completely closed until that catheter is fully extended.

The other prior art patent which should be noted is Cunningham U.S. Pat. No. 4,318,404, which provides "an applicator for a member having a surface," such as a tampon. This applicator works by allowing the surface of the member to be "exposed by relative movement of one of the walls of the applicator with respect to the member." This applicator is not hollow, does not provide for the transfer of fluid, is not doubled along its entire length within the channel, does not remain doubled throughout its operation, must be removed from the channel in an abrasive manner, employs a push-stick arrangement for control, is not intended to be secured or otherwise locked in place, does not indicate to the operator either the position of the end of the tube or the position of the member and the foldout surface provides significant benefit only to the member being exposed and not to the body channel in which it is inserted, since resistance and irritation are produced by both the surface of the member moving against the walls of the body channel as it becomes exposed, as well as resistance caused by the insertion and removal of the applicator. Additionally, it is not intended to be retracted or otherwise controlled and claims a "flexible applicator" and "thin polyresin sleeve" made of a "non-absorbant material".

Other patents which provide a further understanding of the present state of the art and the practical problems and uses of catheters are: Fogarty et al. U.S. Pat. No. 4,271,839, Sheridan U.S. Pat. No. 4,109,659, Kramann et al. U.S. Pat. No. 4,043,345, Silverman U.S Pat. No. 3,168,092, and Fisher U.S. Pat. No. 4,211,234.

The variety of uses for medical catheters, including specific requirements for each type of application, creates many opportunities for new catheter development. This is apparent in the list of related patents presented previously, as each invention attempts to overcome one or two significant problems with its predecessors. In most instances, these solutions are created at the cost of some new complication.

The value of any catheter is directly related to the specific advantages and disadvantages posessed by its design, in combination with the priority of needs of the application for which it is intended. Therefore, in order to assess the potential for any new catheter development, it is necessary to be aware of the most significant problems associated with catheter use today:

Sterility: Maintaining sterility of a conventional catheter, once removed from its sterile package environment, poses many problems. The exterior surface, which will be in contact with body tissue, must be handled and is often exposed to non-sterile surfaces, especially when employed in emergency and field operations.

Insertion: The introduction of a conventional catheter into an opening may prove difficult, due to the size of the opening, lack of definition of the opening and catheter-handling complexities. Proper insertion proves to be a virtually impossible feat at times when the patient is not stationary or cooperative.

Restricted Entry: In certain instances, it is necessary to insert a catheter into a forcibly closed opening or through a channel constriction. This usually requires a special instrument to either pry open the passage, or the use of a guide wire enclosed within the catheter to stiffen the tube so that it may be forced through.

Speed of Use: The need for special handling to ensure sterility, the use of instruments to facilitate insertion, lubricants, and the like, restrict the speed with which a conventional catheter may be employed. This places patients at greater risk, while consuming the otherwise useful time of medical personnel.

Lubricants: Applications of a lubricant to the surface of a conventional catheter prior to introduction, or to the entrance of the channel, in order to facilitate insertion are extremely common. These lubricants are often pushed ahead of the tip of the catheter or wiped off as the catheter enters the channel.

Tissue Trauma: As a result of the need for force in many catheter introduction situations, tissue at the opening and tissue at any point along the channel may be traumatized. This may include irritation, further constriction of the channel, and hemorrhaging.

Infection: Control of bacteria is the most serious problem arising from catheter use today. Conventional catheters tend to drag bacteria and other debris along the surface of the channel as the tube is being pushed in or pulled out. This produces a risk of infection as the tube is inserted, due to likely exposure of the surface of a conventional catheter to an unsterile environment. This movement of a conventional catheter also increases the likelihood of bacteria spreading along the length of the channel.

Direct Placement: Due to the stresses which are caused by the surface of a conventional catheter against adjacent body tissue as it is moved into and out of a channel, conventional catheters are placed so that they lead from the body cavity being served to the exterior surface of the body in as direct a route as possible. This often complicates surgical procedures, placing patients at greater risk.

Channel Obstruction: Conventional catheters often cause great difficulty when they encounter an obstruction while being pushed through a channel. This requires twisting and pushing the tube, or occasionally compromising or abandoning a procedure.

In-channel Situation Analysis: Conventional catheters are incapable of providing the physician with any accurate method of determining the situation within a channel.

Tube Security: Most catheter products on the market today employ a complicated ballon structure which inflates to prevent the distal end of the tube from being pulled out of a cavity, or which inflates within a channel to create resistance against the walls of the channel, thereby preventing undesirable movement. This balloon structure requires a means for controlling inflation and is prone to imperfect operation.

Repositioning: Once a catheter is positioned, it is often desirable to make adjustments in the placement of the tube. Conventional catheters pose all the previously noted movement problems, further complicated by a deterioration in lubricant effectiveness within a short period of time.

Removal: As a conventional catheter is pulled from a channel, shear stresses are created in adjacent body tissue. Additionally, when a flexible conventional catheter is pulled out along a non-linear path, force components transverse to the tube are created, acting to displace body tissue in the vicinity of these bends and further increasing shear stress. The consequences of these forces may include irritation, tissue trauma, further channel constriction and painful, difficult removal of a conventional catheter.

Residual Irrigation: Since many types of conventional catheters must be introduced partialy into a cavity to allow for inflation of a balloon, the drainage function may be impaired. Furthermore, a balloon may actually force matter into the peri-catheter space between the tissue of the channel and the exterior surface of the tube, similar to a plunger.

Pain to the Patient: The ultimate goal of any medical procedure involves the well-being of the patient. Therefore, control of discomfort and pain during the placement, repositioning, continued use and removal of a catheter is most important. Conventional catheters do little to prevent or minimize patient discomfort. In addition to the emotional suffering by a patient, pain and discomfort often place a patient at greater risk, due to conscious resistance to a procedure and continued psychological effect.

Cost Effectiveness: The complexity of many catheters, including design variations which serve only to overcome basic problems, leads to a high initial cost. This is relatively insignificant, however, when compared to the cost associated with subsequent catheter-related complications, which may easily be hundreds or thousands of times the initial price of even the most expensive catheter. Only a catheter which minimizes these subsequent expenses, as well as being reasonably priced, may be considered completely cost effective.

Any catheter which could overcome these problems posses the potential of saving lives. Although this may be considered the primary intent of the invention disclosed by this patent, the significance of commercial value, as measured by the presence of market demand, is recognized as the factor which will ultimately determine the real value of any new product.

One example of the existance of such demand, exposing the immediate need for a new development in the urological catheter segment of the market, is the widespread use of Foley-type tubes. The Foley catheter is one of the most successful medical products in history, selling more units than any other tray or kit on the market today (Frost and Sullivan Report #A1139, *Prepackaged Kits and Trays—Markets in the U.S.*, ©1983). Yet, this is despite some very major problems directly related to its use, such as catheter-induced infection, troubled insertion, and leakage. A study appearing in the *New England Journal of Medicine* and recounted in the Frost & Sullivan Report noted above suggests that over 56,000 deaths per year may be directly attributed to the use of Foley-type tubes in the United States alone. This unacceptable figure becomes even more staggering when other catheter applications and their related consequences are accounted for worldwide. A multiple-use catheter product line, which overcomes most of the present difficulties relating to catheter use, would present a vast opportunity.

OBJECTS OF THE INVENTION

It is an object of this invention to provide a medical catheter which posesses an outer surface which, during all phases of catheter operation, remains stationary relative to the body tissue it comes in contact with.

It is a further object of the invention to provide a medical catheter which minimizes problems relating to infection by reducing bacterial and debris displacement along the length of the body channel during insertion, repositioning, and removal of the catheter.

It is a further object of the invention to provide a medical catheter which, once removed from its sterile package environment, continues to have its sterile surfaces which are to come into contact with internal body tissue remain enclosed, until such time as the catheter is inserted into the body, further reducing risk of infection during emergency, field, and routine operations.

It is a further object of the invention to provide a medical catheter which requires no lubrication applied to its exterior surface for the purpose of facilitating introduction and advancement, simplifying its use and further reducing risk of infection.

It is a further object of the invention to provide a medical catheter which may, if necessary, be advanced into restricted openings and through channel constrictions with relative ease, minimal tissue trauma, and minimal pain to the patient.

It is further object of the invention to provide a medical catheter which, once within the channel, may be advanced or retracted with relative ease and with minimal irritation and trauma to the tissue it comes in contact with and which therefor requires no excessive force, twisting or turning to set it in its desired position.

It is further object of the invention to provide a medical catheter which provides for leveraged control of the advancement and retraction process. This two to one displacement factor—movement of the free end of the tube versus movement of the tip of the tube—allows for more precise placement and also an accurate indication of the length of the tube, while not reducing the speed with which the catheter may be deployed.

It is a further object of the invention to provide a medical catheter which, once introduced into a channel, is capable of directing itself through the channel and around obstacles, without the use of guide instruments, by having its progressing tip roll gently along the contours of the channel while gently displacing aside any small obstacles which may be protruding into the channel.

It is a further object of the invention to provide a medical catheter which is capable of remaining securely placed within a channel, while also being easily repositioned and resecured at any time.

It is a further object of the invention to provide a medical catheter which may be removed with minimal tissue trauma due to adhesion of tissue to the surface of the tube or other resistance, as the tube is not irritably pulled from the channel, dragging against adjacent tissue, but gently peeled away from adjacent tissue at one instant.

It is a further object of the invention to provide a medical catheter which, during removal, collects free-floating matter within, rather than displacing it along the channel of the tube, thereby reducing bacterial dissemination and infection.

It is a further object of the invention to provide a medical catheter which provides the physician with a means to analyze the situation within the channel, as matter collected at any point on the tube directly corresponds to its position within the channel, similar to a sample geologic core. This diagnostic function may be enhanced by variations in the material and texture of the surface of the tube, or by the application of an adhesive coating to the exposed tube surface.

It is a further object of the invention to provide a medical catheter which may be led from within the body to the surface of the body in a tortuous manner, around sensitive organs or other obstacles, without concern for stress to such organs from the tube during removal, greatly simplifying certain catheter placement procedures, while making others possible.

It is a further object of this invention to provide a medical catheter into which may be placed a balloon, medicated pad, adhesive substance, biopsy probe, radiation pellet, or other such instrument or application, prior to the insertion of the catheter into the body channel, to be exposed only at such time as the tube is extended to its desired position within the channel, thereby eliminating undesirable contact of such hazardous inserts with other tissue surfaces along the length of the channel.

It is a further object of this invention to provide a medical catheter which posesses a design readily adaptable to most catheter applications through simple variation in diameter, length, surface characteristics, materials, and other component features during manufacture.

It is ultimate object of the invention to provide a medical catheter which reduces pain, trauma, and risk to the patient, reduces operational complexity and handling time requirements for the physician, operates with minimal chance for malfunction, is extremely cost effective and saves lives.

BRIEF DESCRIPTION OF THE DRAWINGS

FIG. 1a is a front view of a preferred embodiment of a catheter of the invention with the catheter tube almost completely extended.

FIG. 1b is a side view of the catheter shown in FIG. 1a, looking from the right-hand side of FIG. 1a.

FIG. 1c is a sectional view of a tube portion of the catheter in FIG. 1a, taken at arrows c—c in FIG. 1a.

DETAILED DESCRIPTION OF THE INVENTION

The present invention is directed to a new type of catheter, referred to as an "externally-based inversionary tube".

Refering to FIGS. 1a through 1d, the catheter of this invention is designated generally 7 and includes a tube designated generally 100. Tube 100 is made of a material which may be varied in its circumference. Tube 100 has an inner portion designated generally 25 and outer portion designated generally 24, connected by fold designated generally 11. Channel of tube 100 is designated generally 12. Inner portion 25 of tube 100 is divided into two surfaces, a center-facing surface designated generally 13 and an outer-facing surface designated generally 15. Outer portion 24 of tube 100 is also divided into two surfaces, a center-facing surface designated generally 16 and an outer-facing surface designated generally 14.

Outer-facing surface 14 of outer portion 24 and innerfacing surface 13 of inner portion 25 are a continuous surface divided by an imaginary line at fold 11 of tube 100. Similarly, inner-facing surface 16 of outer portion 24 and outer-facing surface 15 of inner portion 25 are a continuous surface divided by an imaginary line at fold 11 of tube 100. A segment of the end of outer portion 24 of tube 100 opposite fold 11 is permanently attached to a handhold designated generally 9. Handhold 9 has a textured outer surface designated generally 8 and an internal channel designated generally 20. A segment of tube 100 extending from handhold 9 in direction of fold 11 is designated generally as a far end 5 of catheter 7. A segment of inner portion 25 of tube 100 extending out from handhold 9 in direction opposite fold 11 is designated generally as a free end 2 of catheter 7. Inner portion 25 of tube 100 extends from free end 2 of catheter 7 into channel 20 of handhold 9 where inner portion 25 is adjacent to and slidably resident within outer portion 24 of tube 100. Inner portion 25 extends through handhold 9, becoming part of far end 5 of catheter 7. At fold 11, inner portion 25 folds back onto itself and becomes outer portion 24 of tube 100. Outer portion 24 extends back into handhold 9 where it is permanently attached to handhold 9.

Tube 100 of catheter 7 is made of a material capable of being varied in circumference just enough that tube 100 may be doubled over itself, as shown in FIGS. 1a through 1d, without significant distortion at fold 11 and without causing inner portion 25 of tube 100 to kink or collapse inward relative to outer portion 24 of tube 100. Tube 100 of catheter 7 is preferably flexible along its length for most medical applications. Exact material specifications are determined by the requirements of the application for which any particular catheter is intended. However, desired length, outside diameter of tube 100, and pressures within the body channel are three primary considerations. Special characteristics required of the material and design of tube 100, such as high surface resistance, high temperature or chemical-specific resistance, or absorbtion qualities, must also be considered. The material of which tube 100 of catheter 7 is made must also be sterilizable and acceptable for its intended surgical application. Silicone is one material for tube 100 which satisfies these characteristics.

In addition to tube 100, a thin coating of a lubricating substance may be bonded to enclosed surface 15, 16. This creates a lubricated interface between inner portion 25 of tube 100 and outer portion 24 of tube 100. This interface allows inner portion 25 of tube 100 to slidably reside within adjacent outer portion 24 of tube 100. A silicone tube with a teflon coated surface is preferred. One embodiment of catheter 7 of the invention includes a silicone tube with an outer diameter of 1.0 centimeters and a wall thickness of 0.15 centimeters.

As inner portion 25 at free end 2 is urged in a direction towards handhold 9 while handhold 9 is held stationary, entire inner portion 25, slidably residing within outer portion 24, moves in a direction towards far end 5 and relative to stationary handhold 9 and attached outer portion 24 of tube 100. As any section of inner portion 25 of tube 100 reaches fold 11, the section rolls out at fold 11 and becomes newly formed outer portion 24. This elongates far end 5 of catheter 7 without movement of outer portion 24 or outer surface 14 of catheter 7, except for gentle continuous rolling action of tube 100 at fold 11. Overall length of catheter 7 shortens as far end 5 elongates, as a segment of inner portion 25 of tube 100 becomes doubled at far end 5.

Similarly, as inner portion 25 at free end 2 is urged in a direction away from handhold 9 while handhold 9 is held stationary, entire inner portion 25, slidably residing within outer portion 24, moves in a direction towards free end 2, relative to stationary handhold 9 and attached outer portion 24 of tube 100. As inner portion 25 moves, forces created in tube 100 resolve themselves as outer portion 24 rolls into itself at fold 11 becoming newly formed inner portion 25. This shortens far end 5 of catheter 7 without movement of outer portion 24 or outer surface 14 of catheter 7, except for gentle continuous rolling action of tube 100 at fold 11. Overall length of catheter 7 lengthens as far end 5 shortens, as doubled segment of far end 5 becomes inner portion 25.

In addition to tube 100 and handhold 9, the preferred embodiment of catheter 7 includes a locking ring mechanism designated generally 6, an end cap designated generally 1 with a hole designated generally 17 and a stopper ring designated generally 3. Numerals and indicia designated generally 4, 10 may be printed on surfaces 13, 14, 15, 16 of tube 100 in order to provide the operator with a constant indication of the exact length and position of far end 5 and end defined by fold 11 of catheter 7. Markings 4 on enclosed surface 15, 16 are visible at free end 2 of catheter 7 and markings 10 on exposed surface 13, 14 are visible at far end 5 of catheter 7.

Figure 2A:
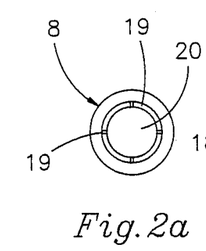
FIG. 2a is a side view of the structure illustrated in FIG. 2b, looking from the left-hand side of FIG. 2b.
Figure 2B:
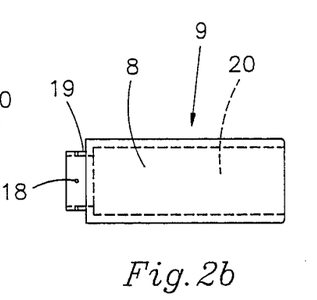
FIG. 2b is a front view of a handhold portion of the catheter of FIGS. 1a through 1d.
Figure 2C:
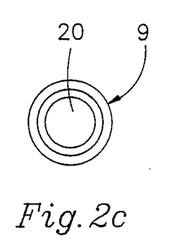
FIG. 2c is a side view of the structure illustrated in FIG. 2b, looking from the right-hand side of FIG. 2b.

Referring to FIGS. 2a through 2c, handhold 9 has textured surface 8 and internal channel 20. Internal channel 20 is sized for most of its length to fit securely over end of outer portion 24 of tube 100. Remaining segment of length of channel 20 of handhold 9, shown at the left of FIG. 2b, is sized to allow for free inward and outward passage of inner portion 25 of tube 100. Extended portion designated generally 19 of handhold 9 has a smooth outer surface and an outer diameter slightly less than the inner diameter of the locking ring designated generally 6 shown in FIGS. 3a and 3b. Extended portion 19 has small holes designated generally 18 which are shown in FIGS. 4a and 4b.

Figure 3A:
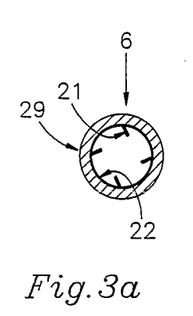
FIG. 3a is a side view of a locking ring structure illustrated in FIG. 3b, looking from the left-hand side of FIG. 3b.
Figure 3B:
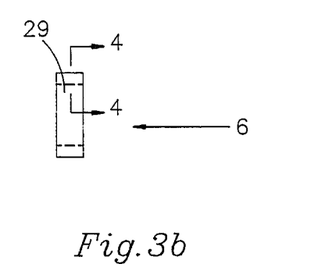
FIG. 3b is a front view of a locking ring structure portion of the catheter of FIGS. 1a through 1d.

Referring to FIGS. 3a and 3b, locking ring 6 includes a textured outer surface designated generally 29, a smooth inner surface designated generally 22 and four finger members designated generally 21 which respectively correspond to the four holes 18 in extended portion 19 of handhold 9.

Figures 1A, 1B:
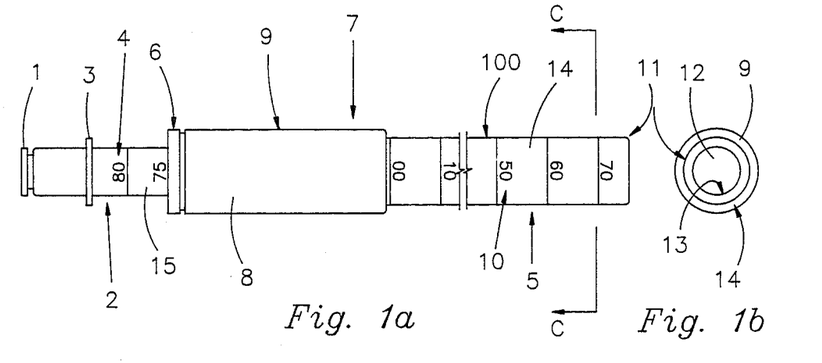
Figure 1C:
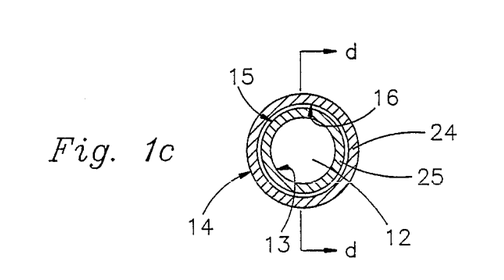
Figure 1D:
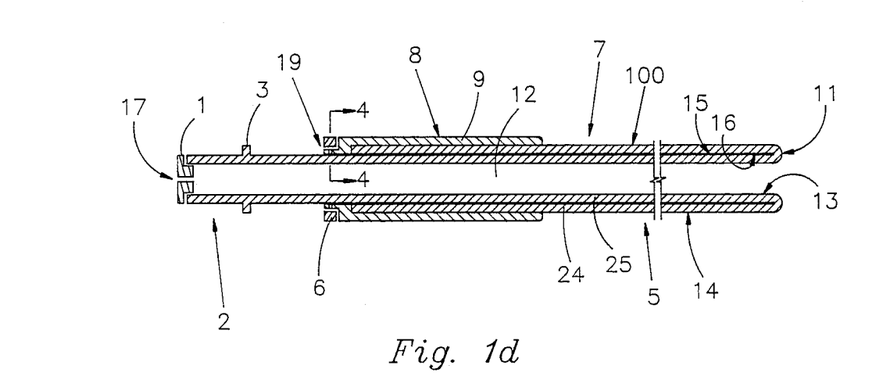
FIG. 1d is a sectional view of the catheter of FIGS. 1a through 1c, taken at arrows d—d in FIG. 1c.
Figure 4A:
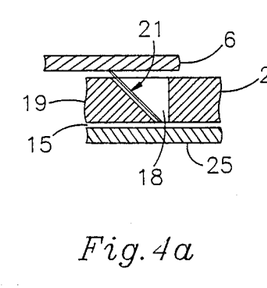
FIG. 4a is a partial sectional view of a segment of the locking ring structure portion shown in FIGS. 3a and 3b of the catheter of FIGS. 1a through 1d, taken at arrows 4—4 in FIG. 3b and in FIG. 1d, with the locking ring structure illustrated in position over the extended portion of the handhold shown in FIGS. 2a and 2b and with the inner portion of the tube of the catheter extended through the handhold barrel, showing the locking structure disengaged from the tube.
Figure 4B:
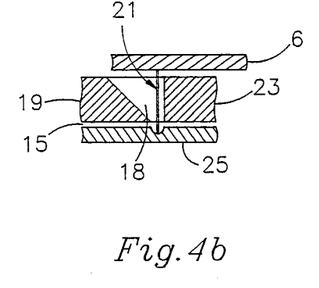
FIG. 4b is a partial sectional view of a segment of the locking ring structure portion shown in FIGS. 3a and 3b of the catheter of FIGS. 1a through 1d, taken at arrows 4—4 in FIG. 3b and in FIG. 1d, with the locking ring structure illustrated in position over the extended portion of the handhold shown in FIGS. 2a and 2b and with the inner portion of the tube of the catheter extended through the handhold barrel, showing the locking structure engaged with the tube.

Referring to FIGS. 4a and 4b, locking ring 6 is positioned over extended portion 19 of handhold 9 with finger members 21 positioned within small holes 18, as shown also in FIG. 1d. FIG. 4a shows locking ring 6 with finger member 21 retracted within hole 18. As locking ring 6 is turned clockwise while handhold 9 is held stationary, finger member 21 is deflected off a far wall designated generally 23 of hole 18 and finger member 21 moves in a direction towards the center of internal channel 20. As finger member 21 enters internal channel 20, finger member 21 contacts outer surface 15 of inner portion 25 of tube 100, as shown in FIG. 4b, thereby preventing inner portion 25 from moving into or out of handhold 9, as shown in FIG. 4b. As locking ring 6 is turned in counter-clockwise while handhold 9 is held stationary, finger members 21 retract back into holes 18, thereby allowing inner portion 25 of tube 100 to move freely.

Figures 5A, 5B, 6A, 6B:
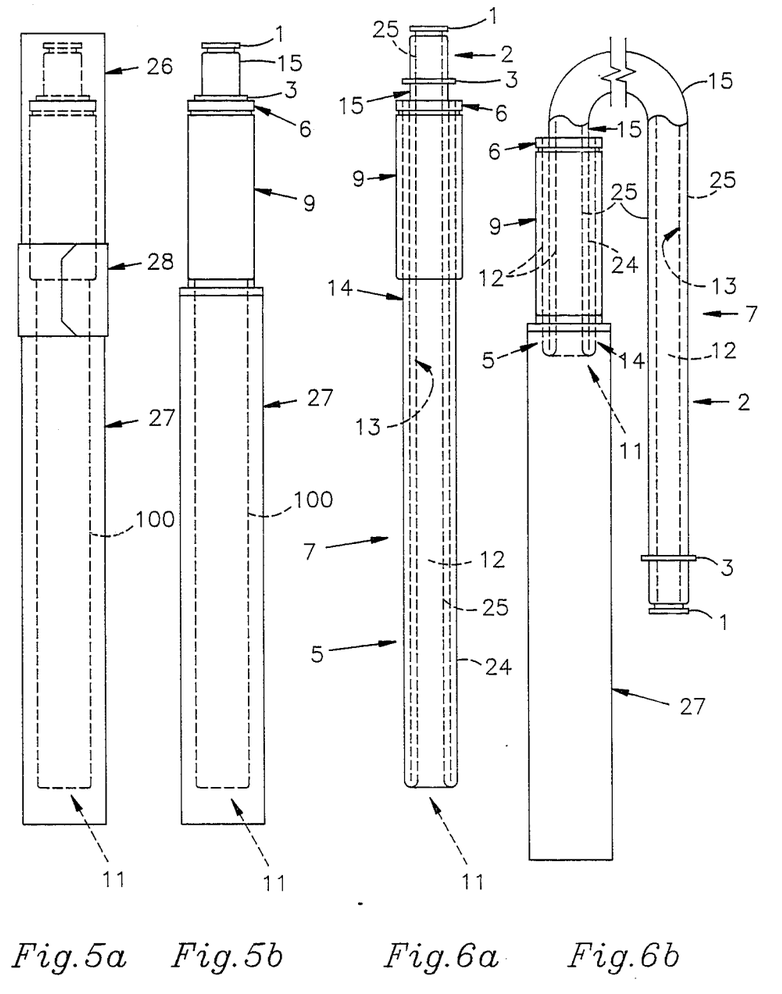
FIG. 5a is a front view of a container housing the catheter of FIGS. 1a through 1d, with the outline of the catheter shown in dotted lines.
FIG. 5b is a front view of the catheter of FIGS. 1a through 1d and FIG. 5a, showing a seal and a top portion of the catheter container removed, exposing a portion of the catheter.
FIG. 6a is a front view of the catheter of FIGS. 1a through 1d and FIGS. 5a and 5b, showing the catheter removed from its container in a fully extended configuration and showing the inner portion, outer portion, and inversionally folded tip of the catheter tube in dotted lines.
FIG. 6b is a front view of the catheter of FIGS. 1a through 1d and FIGS. 5a and 5b, showing the catheter essentially removed from its container in a nearly fully retracted configuration and showing the inner portion, outer portion, and inversionally folded tip of the catheter tube in dotted lines.

Referring to FIGS. 5a and 5b, catheter 7 is shown positioned within bottom portion 27 of a catheter container. FIG. 5a also shows a top portion 26 and a safety seal 28 of the catheter container. Catheter 7 is stored in its sterile container 26, 27 with locking ring 6 turned to the "free" position shown in FIG. 4a.

Referring to FIGS. 6a and 6b, catheter 7 is shown in two configurations. FIG. 6a shows catheter 7 with far end 5 of tube 100 nearly fully extended, and FIG. 6b shows catheter 7 with far end 5 of tube 100 almost completely retracted.

Figures 7A, 7B, 7C:
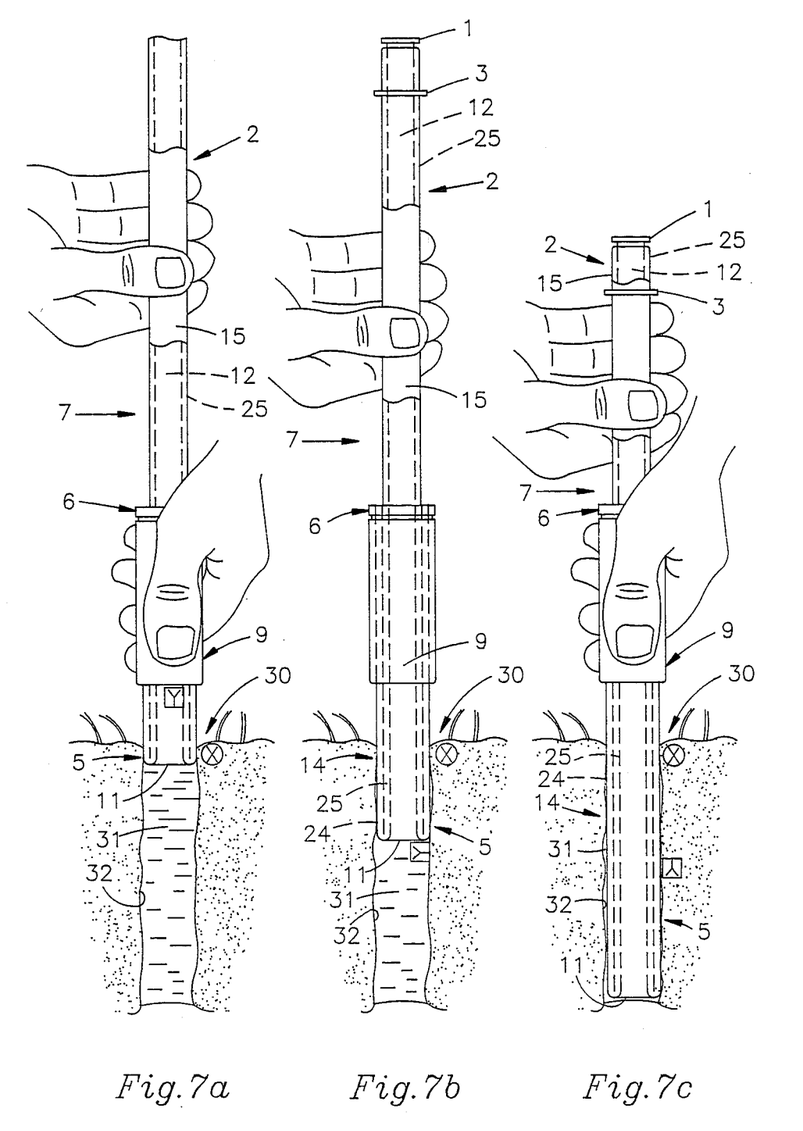
FIG. 7a is a front view of the catheter of FIGS. 1a through 1d, similar to FIGS. 7b and 7c, but showing the catheter in a nearly fully retracted configuration with the catheter tip positioned at a body opening entrance, and showing the inner portion, outer portion, and inversionally folded tip of the catheter tube in dotted lines.
FIG. 7b is a front view of the catheter of FIGS. 1a through 1d, similar to FIGS. 7a and 7c, but showing the catheter in a partially extended configuration with the catheter tip and a portion of the inversionally folded catheter tube within the body and showing the inner portion, outer portion, and inversionally folded tip of the catheter tube in dotted lines.
FIG. 7c is a front view of the catheter of FIGS. 1a through 1d, similar to FIGS. 7a and 7b, but showing the catheter extended to a desired length with its inversionally folded tip portion of the catheter tube at a desired location within the body and showing the inner portion, outer portion, and inversionally folded tip of the catheter tube in dotted lines.

Referring to FIGS. 7a through 7c, far end 5 of tube 100 of catheter 7 is shown in various positions within a channel designated generally 31 having an opening designated generally 30 and a surface designated generally 32. Encircled "X" and boxed "Y" representing fixed points on the surface of tube 100, as inner portion 25 at free end 2 is urged into and out of stationary handhold 9.

Figure 8:
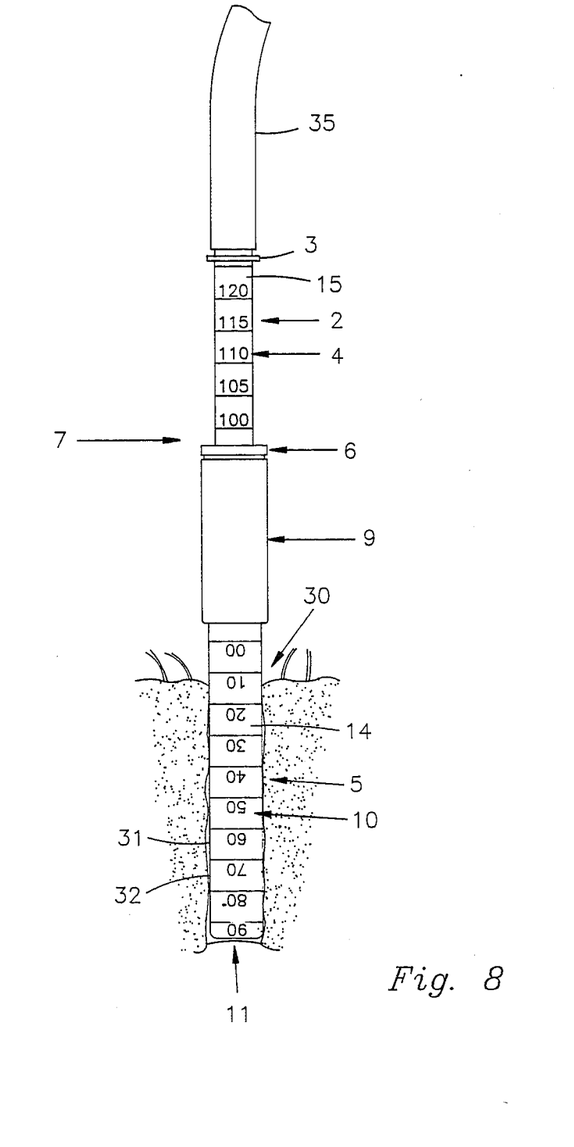
FIG. 8 is a front view of the catheter of FIGS. 1a through 1d, similar to FIGS. 7a through 7c, showing the catheter being used to transport fluid relative to the body and showing the corresponding enclosed surface and exposed surface indicia.

Referring to FIG. 8, catheter 7 is in a desired position within channel 31 transporting fluid relative to body tissue.

Figure 9A:
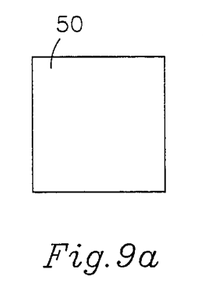
FIG. 9a schematically illustrates the preferred smooth outer surface of the tube portion of the catheter of the invention.
Figure 9B:
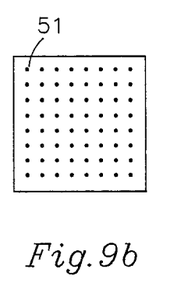
FIG. 9b schematically illustrates an alternate outer surface of the tube portion of the catheter of the invention where the outer surface includes a series of spaced apart protuberances projecting outwardly.
Figure 9C:
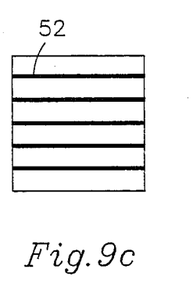
FIG. 9c schematically illustrates another alternate outer surface of the tube portion of the catheter of the invention where the outer surface includes outwardly projecting circumferential ribs.
Figure 9D:
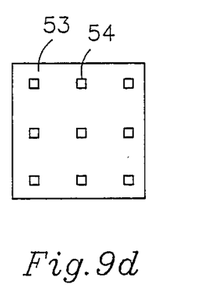
FIG. 9d schematically illustrates yet another alternate outer surface of the tube portion of the catheter of the invention where the outer surface includes a series of spaced apart raised collection devices having concave outwardly facing surfaces.

Referring to FIGS. 9a through 9d, variations in exposed surface 13, 14 of tube 100 of catheter 7 may be desirable for certain applications, to increase resistance of tube 100 relative to surface of body tissue 32, increase the outer diameter of tube 100 at certain points, collect matter from surface of body tissue 32 which tube 100 of catheter 7 contacts or provide an exterior channel. FIG. 9a shows a smooth surface designated generally 50. FIG. 9b shows a surface with raised bumps or prongs designated generally 51. FIG. 9c shows a surface with circumferential ribs designated generally 52. FIG. 9d shows a specialized surface with raised collecting devices designated generally 53, having concave outwardly facing surfaces designated generally 54.

There are two methods of employing catheter 7. The first of these involves removal of catheter 7 from container 27 in a nearly fully extended position. This is done when there is direct access to the cavity in which end defined by fold 11 is to be positioned. One example of this might be placement of a drainage tube into a body cavity during surgery. In this instance, package seal 28 and package top 26 are removed. Catheter 7 is preferably retracted a small amount, so that it may be later extended if necessary, by an operator pulling on exposed free end 2 of inner portion 25 of tube 100 while holding handhold 9 stationary. Locking ring 6 is turned to the "locked" position shown in FIG. 4b to prevent accidental advancement and retraction of far end 5 of tube 100. The entire catheter 7 is then taken from container 27 by pulling on handhold 9 while holding container 27 stationary. This allows catheter 7 to be removed in a nearly fully extended position as shown in FIG. 6a. The end defined by fold 11 at far end 5 of tube 100 of catheter 7 is then directed into the cavity while handhold 6 and free end 2 of tube 100 remain outside the body. Catheter 7 may then be secured in place by firmly wrapping sutures around a section of tube 100 at far end 5 and suturing through adjacent body tissue. Once surgery is complete, tube 100 extends from inside the body cavity through body channel 31 to surface of body 30 and outside the body. Free end 2 of tube 100 of catheter 7 may be attached to connecting tube 35 as shown in FIG. 8 leading to a drainage bag or other equipment.

When this method is employed, the primary advantages of catheter 7 become apparent during repositioning and removal. To advance or retract catheter 7 after surgery is complete and catheter 7 is securely sutured in place, the operator turns locking ring 6 located at the back of handhold unit 9 to the "free" position shown in FIG. 4a and, while holding handhold unit 9 stationary, pushes or pulls on free end 2 of inner portion 25 of tube 100 to elongate or shorten far end 5 of tube 100 of catheter 7, as desired. Locking ring 6 is then returned to the "locked" position. Since outer surface 14 of tube 100 of catheter 7 remains stationary relative to contacted body tissue surface 32, end defined by fold 11 of tube 100 may be rollingly advanced and retracted without disturbing sutures or causing shear stresses or irritation with respect to body tissue surface 32. Furthermore, during removal of catheter 7, it is not necessary to surgically access the sutures to cut them free from catheter 7, or to attempt to pull tube 100 out from wrapped sutures. Retraction of far end 5 of tube 100 of catheter 7 and removal from channel 31 are shown in FIGS. 7c, 7b and 7a, in that respective sequence.

The second method of employing catheter 7 involves removal of catheter 7 from container 27 in a fully retracted position. This is done when far end 5 of tube 100 of catheter 7 is to be inserted into a channel. One example of this might be when a catheter is inserted through the urethera to the bladder. In this situation, the operator pulls on free end 2 of inner portion 25 of tube 100 while catheter 7 is in container 27. This shortens far end 5 of catheter 7 as shown in FIG. 6b. Once this is done, the operator grasps handhold 9 while holding container 27 stationary and pulls entire catheter 7 from container 27. Catheter 7 is now ready to be inserted into channel 31. Note that surface 13 of catheter 7 which will come into contact with body tissue 32 as the catheter is advanced within channel 31 is enclosed, unlikely to be exposed to bacteria and other matter.

To insert catheter 7 into channel 31, the operator positions end defined by fold 11 of catheter 7, either at opening 30 of channel 31 or slightly into opening 30 of channel 31 by maneuvering handhold 9. Once this is done, the operator pushes free end 2 of inner portion 25 of tube 100 of catheter 7 forward, in a direction towards handhold 9. This will cause far end 5 of tube 100 of catheter 7 to elongate and advance into channel 31. Notice that elongation of far end 5 of tube 100 of catheter 7 and advancement into channel 31 occurs without relative movement between surface 14 of tube 100 of catheter 7 and body tissue surface 32 of channel 31. Once end defined by fold 11 at far end 5 of tube 100 of catheter 7 is in a desired position, locking ring 6 is turned to the "locked" position shown in FIG. 4b to prevent far end 5 of tube 100 of catheter 7 from accidental advancement and retraction. Elongation of far end 5 of catheter 7 and advancement into channel 31 are shown in FIG. 7a, 7b and 7c, in that respective sequence.

During continued use of catheter 7, far end 5 may be repositioned without concern for tissue adhesion or lubricant deterioration. The operator turns locking ring 6 located on the back of handhold 9 to the "free" position and, while holding handhold unit 9 stationary, pushes or pulls on free end 2 of inner portion 25 of tube 100 to elongate or shorten far end 5 of tube 100 of catheter 7, as desired. Locking ring 6 is then returned to the "locked" position.

Removal of catheter 7 from channel 31 is performed in a similar manner, by turning locking ring 6 to the "free" position and then pulling on free end 2 of inner portion 25 the tube 100 in the direction away from handhold 9, while holding handhold 9 stationary, until far end 5 of tube 100 of catheter 7 is clear of body channel opening 30. Notice retraction of far end 5 of tube 100 of catheter 7 from channel 31 occurs without relative movement between outer surface 14 of tube 100 and body tissue surface 32 along channel 31. Catheter 7 may be disposed of in this retracted configuration, with the contaminated inner surface 13 enclosed. Retraction of far end 5 of tube 100 of catheter 7 and removal from channel 31 are shown in FIGS. 7c, 7b and 7a, in that respective sequence.

The most significant advantages of catheter 7 over conventional catheters include:

Sterility: When catheter 7 is removed from container 27 in a retracted configuration, surface 13 which will contact body tissue is enclosed, unlikely to be exposed to unsterile surfaces, minimizing the risk of infection.

Insertion: Far end 5 of tube 100 of catheter 7 is readily advanced into openings and channels, including those which may be constricted, due to the rolling action at end defined by fold 11 and lack of movement and shear stresses created by outer surface 14.

Advancement: As catheter 7 encounters bends and resistance in a channel, far end 5 of tube 100 of catheter 7 continues advancing and does not flex, as stresses created by catheter 7 during advancement are resolved at the lubricated interface between outer portion 24 and inner portion 25.

Speed of Use: No prep kits or trays to pull apart, no sterile pads, no gloves to put on, no lubricants to apply and no delicate tube handling procedures mean quick deployment and use of catheter 7.

Tissue Trauma: As outer surface 14 of tube 100 of catheter 7 does not move relative to adjacent body tissue, except for gentle rolling action, tissue irritation and trauma resulting from shear stresses is reduced or eliminated.

Infection: Catheter 7 cannot drag bacteria into a channel since it is not pushed in like a conventional catheter. So long as surface 13, which contacts body tissue as catheter 7 is elongated and advanced, is sterile, it is nearly impossible for catheter 7 to introduce bacteria into a channel.

Routing of Catheter: Catheter 7 may be positioned in and readily removed from winding passages, as forces transverse to catheter 7 and also shear stresses are resolved at the lubricated interface between outer portion 24 and inner portion 25.

Channel Obstructions: Should the advancing tip and fold 11 of catheter 7 encounter a small obstruction within a channel, the rolling action of end defined by fold 11 of catheter 7 will gently displace aside such obstruction, rather than jam or shear against it.

Specific Access: Any point on the outer surface 14 of catheter 7 comes into contact with a single predeterminable point of body tissue in the channel. This may be advantageous for the controlled introduction and placement of substances and devices.

Catheter Security: Catheter 7, because it does not require lubricants applied to its outer surface, remains in place within a channel by surface resistance. Also, variations in outer surface 14 of catheter 7 may enhance the security of catheter 7 within a channel.

Repositioning: Catheter 7 may be repositioned and resecured at any time, regardless of sutures around far end 5 of tube 100, indirect placement of tube 100, or other resistance from a channel surface.

Removal: No relative movement between outer surface 14 of catheter 7 and body tissue surface along a channel, except for a gentle peeling action at end defined by fold 11, allows for simple, easy retraction and removal of catheter 7 from a channel. Shear stresses and other forces are resolved within tube 100 of catheter 7.

Irrigation: Catheter 7 may be introduced just into the opening of a cavity, allowing for total drainage. Additionally, a surface texture variation, such as a circumferenial rib 52, may help seal catheter 7 with respect to cavity opening, preventing undersirable leakage of fluid into the peri-catheter space between catheter 7 and body tissue in channel.

Catheter-Induced Pain: Catheter 7, due to the virtual elimination of shear stresses against body tissue and a significant reduction in catheter forces transverse to a channel which are resolved within tube 100 of catheter 7, catheter-induced pain and suffering experienced by a patient are minimized, reducing the overall risk of a procedure.

Cost Effectiveness: The simplicity of catheter 7, including no need for ancillary objects such as sterile pads, gloves, lubricants, and the like, results in a relatively low manufacuring cost. Furthermore, the risk of subsequent catheter-related complications is drastically reduced as a result of the many benefits provided by catheter 7. This savings, in both financial terms and reduced suffering and lives saved, is likely to be many times greater than the initial cost of catheter 7.

The applications for which these benefits provided by catheter 7 prove advantageous are numerous, especially in the medical field where any single benefit could mean the difference between life and death, in the extreme, or at very least the difference between dollars spent and dollars saved. The following is a brief list of sample medical applications:

Urinary Tract Catherization: This catheter 7 is especially well suited for this application, eliminating many of the potential dangers of Foley-type tubes. This catheter 7 may be inserted with greater speed and ease, less pain, minimized tissue trauma, less risk of infection, greater control, and fewer leakage problems. Additionally, it may be securely positioned without the complexities of a balloon, repositioned and resecured with ease at any time, retracted for channel irrigation, or removed with minimal effort and trauma. At present, the Foley-type catheter is most commonly used for this procedure. Yet, as discussed in an article by Calvin M. Kunin, M.D., appearing in May 15, 1984 issue of *The American Journal of Medicine*, entitled "Genital Urinary Infections in the Patient at Risk: Extrinsic Risk Factors", catheter-induced infection continues to be the most common problem faced by hospitals, with over one-third of all nosocomial infections relating to the urinary tract. With this procedure being performed tens of millions of times every year, it is believed that this catheter 7 is capable of reducing and eliminating many of these problems, thereby reducing suffering and saving thousands of lives.

Tracheal Intubation: It is often necessary to introduce a tube into the trachea to provide a clear channel for transfer of gases. This procedure may be performed in emergency situations where the trachea is obstructed, or prior to an operation, to establish an easily accessible airway. Especially in the former instance, speed and ease of performance are essential. This catheter 7 posesses many benefits which make it useful for tracheal intubation. Primarily, because of the rolling action of fold 11 at distal end 5, this catheter 7 may be introduced into partially-closed openings and channels, while self-directing itself along the channel and minimizing both irritation and trauma to adjacent tissue. For example, this catheter overcomes the problems associated with "seized" vocal cords, as the end defined by fold 11 of this catheter 7 gently pries through this channel restriction, rather than jamming and having to be forced through with the possibility of damage. Also, for pre-operative applications, this catheter 7 may be introduced without the aid of an introducer or guide, with less irritation, trauma and pain for the patient. A variation specifically for this purpose may include an inner portion 25 segment which is curved and hard, similar to present tracheal tube designs, and a softer flexible outer portion 24 segment, thereby providing a specialized version of the catheter 7 presently disclosed.

Site Drainage: Very often, infections passed off as "post-op" may be attributed to catheter use. The advantages of this catheter 7 most relevant to site application include initial sterility factors, ability to readily reposition the catheter 7 at any time, catheter 7 security, lack of bacterial displacement by the exposed surface 13,14 of catheter 7, indirect placement ability, non-abrasive removal, and channel situation analysis capability. Ribbing 52 on the outer surface 14 of tube 100 may provide additional security and a means of minimizing movement of matter within the peri-catheter space.

Feeding Tube: Another common application for which this catheter 7 may prove beneficial is that of a feeding tube. The primary advantages of this catheter 7 over conventional catheters are its ability to be advanced within the channel without relative movement between tissue and tube surfaces, as well as its self-directing capabilities, which allow it to be positioned more easily and securely than conventional catheters. Variations which may be desired for this application include radially projecting prongs 51 which become exposed within the channel to help secure the tube in its desired position, ribbing 52 and other exposed surface 13,14 texture variations as shown in FIGS. 9b through 9d.

Figure 10A:
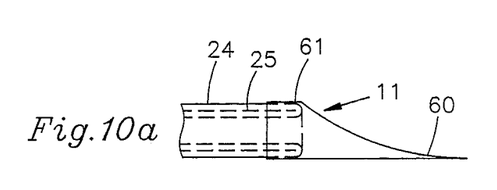
FIG. 10a is a side view of the inversionally folded catheter tube having a curved scalped affixed to the tube exterior, and showing the inner portion, outer portion, and inversionally folded tip of the catheter tube in dotted lines, with the tip of the catheter tube not extended beyond the blade.
Figure 10B:
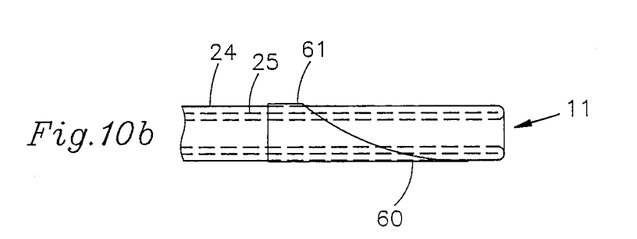
FIG. 10b is a side view similar to FIG. 10a showing the inversionally folded catheter tube, with a portion of the curved scalpel affixed to the tube exterior, and showing the inner portion, outer portion, and inversionally folded tip of the catheter tube in dotted lines, with the catheter tube extended beyond the scalpel.

Roll-In Bypass: This is an application which is believed to be unique and only possible with this catheter 7. In an instance when a large area is traumatized and vessels are torn or otherwise severed, it may be desirable to immediately reconnect these passageways. As a result of the characteristics posessed by this catheter 7, these severed vessels may be catheterized by clamping to eliminate any flow, cutting the loose end of the vessel to create a well-defined opening, and then rolling in the disclosed catheter 7 of proper size. Furthermore, two or more such catheters 7 may be connected to provide a link between the loose ends of vessels. In another variation for this application, a scalpel blade 60 secured to the far end 5 of this catheter 7 may be employed to puncture the wall of a vessel in order to facilitate insertion. This arrangement is shown in FIGS. 10a and 10b. Once this catheter 7 is inserted and advanced, blade 60 lies flat against outer surface 14 of tube 100 of catheter 7, possibly within recesses in the catheter wall 24.

Biopsy: Another unique application for this catheter 7 is biopsying tissue along a channel, whether this channel be natural, or surgically created. As catheter 7 is advanced, and end defined by fold 11 rolls in, any point on outer surface 14 of tube 100 comes into contact with only one point on the surface of the channel. With variations of exposed surface 14, such as an adhesive coating or strategically placed small hollow puncture devices 53 shown in FIG. 9d, samples may be collected for analysis. Furthermore, the position of each biopsy may be readily ascertained.

Balloons: Such devices are most often employed to secure a catheter in its desired position. However, balloons are also used for a variety of other purposes, including forcing matter to the side of the channel.

When a conventional catheter with a balloon is used for this purpose, the entire assembly must be forced through the channel, often creating problems or restricting a procedure. With this catheter 7, the balloon, a unit separate from catheter 7, may be-placed into internal channel 12 of catheter 7 prior to insertion into body channel 31. Once the balloon is exposed at its desired position, it may be inflated. Then, catheter 7, with or without the balloon, may be withdrawn. This process eliminates the tissue abrasion and irritation problems associated with conventional balloon catheter use.

Medicinal/Radiation Application: Due to the characteristics of this catheter 7, medicated or irradiated pads may be strategically placed within channel 12 of catheter 7 prior to insertion into the body, allowing these pads to contact certain predetermined tissue surfaces, while not affecting others. For example, where local radiation is desired for cancer treatment, a catheter with a lead-lined enclosed surface 15,16 may deliver such treatment to a very specific area within a natural or surgically created channel, without unnecessarily endangering uninvolved tissue.

Absorbative Insert: In this application, an embodiment of catheter 7 posesses a tube 100 made of an absorbant material, but otherwise having the characteristics of tube 100 previously described. This embodiment of catheter 7 may be introduced into a channel for the purpose of absorbing fluid which contacts outer surface 14, rather than for purpose of transporting fluid within a channel described by tube 100. This embodiment preferably has inner portion 25 and outer portion 24 of sufficient wall thickness to virtually eliminate interior channel 12. Since most absorbant materials are highly abrasive as a result of their porous nature, this variation of catheter 7 may overcome consequences associated with the insertion and removal of such a material into a body channel.

Although the procedures for this catheter 7 are similar in many regards, each necessitates a unique set of specifications, including variations in diameter, length, and material characteristics. Yet, even the most diverse application continues to provide the many benefits and advantages of the basic design, maximizing the possibility of improving the quality of medical care, reducing pain, and ultimately saving lives.

What is claimed is:

1. An externally based inversionary tube for use as a catheter and the like, comprising:
   a. a grip member having a first passageway therethrough;
   b. a hollow tube secured to said grip member and having the tube interior aligned with said first passageway through said grip member;
   c. said hollow tube being inwardly folded upon itself to provide a telescoping tube assembly having inner and outer tubular portions of variable length with a first extremity of said tube secured to said grip member, with a second extremity of said tube defining an end of said inner portion and extending outwardly from said first passageway in a direction oppositely to said direction of tube assembly emergence from said grip towards said position of tube inversion at which said tube is folded upon itself, with said inner and outer tubular portions being connected by said portion of said tube which is folded upon itself, with a portion of said inner tube adjacent said portion which is folded upon itself annularly expanding and successively defining said portion of said tube which is folded upon itself and a portion of said outer tube adjacent said portion of said tube which is folded upon itself as said inner tubular portion is urged through said grip member in a direction to reduce length of said inner tubular member, towards said area at which said tube is folded upon itself; and
   d. means for locking said inner tubular member passing through said grip member at a variably selected position relative to said grip member, wherein said locking means further comprises:
      i. an annular ring disposed about and spaced from said tube, moveable axially relative to said tube;
      ii. resilient finger means for releasably engaging said tube, extending radially inwardly from said ring towards said tube at an angle to the axis of said tube, having length greater than distance by which said annular ring is spaced from said inner tube portion;
      iii. sleeve means between said ring and said tube;
      iv. said sleeve means having a radial second passageway therethrough, said radial second passageway defining orifices at respective outer and inner surfaces of said sleeve and receiving said finger means, said radial second passageway tapering from said outer surface orifice to said inner surface orifice so that said outer surface orifice is larger than said inner surface orifice to permit said finger means to remain in a relatively unflexed condition in a first position of said annular ring relative to said tube and causing said finger means to contact a wall portion of said second passageway and be deflected radially inwardly thereby exiting said second passageway at said inner surface orifice of said sleeve and intersectingly contacting said tube to grippingly engage and immobilize said tube relative to said ring upon movement of said annular ring axially relative to said tube.

2. The inversionary tube of claim 1 wherein said passageway has a wall portion perpendicular to the axis of said tube.

3. An externally based inversionary tube for use as a catheter and the like, comprising:
 a. a grip member having a first passageway therethrough;
 b. a hollow tube secured to said grip member and having the tube interior aligned with said first passageway through said grip member;
 c. said hollow tube being inwardly folded upon itself to provide a telescoping tube assembly having inner and outer tubular portions of variable length with a first extremity of said tube secured to said grip member, with a second extremity of said tube defining an end of said inner portion and extending outwardly from said first passageway in a direction oppositely to said direction of tube assembly emergence from said grip towards said position of tube inversion at which said tube is folded upon itself, with said inner and outer tubular portions being connected by said portion of said tube which is folded upon itself, with a portion of said inner tube adjacent said portion which is folded upon itself annularly expanding and successively defining said portion of said tube which is folded upon itself and a portion of said outer tube adjacent said portion of said tube which is folded upon itself as said inner tubular portion is urged through said grip member in a direction to reduce length of said inner tubular member, towards said area at which said tube is folded upon itself; and
 d. means for locking said inner tubular member passing through said grip member at a variably selected position relative to said grip member, wherein said locking means further comprises:
  i. an annular ring disposed about, spaced from and being axially rotatable relative to said tube;
  ii. resilient finger means for releasably engaging said tube, extending from said ring inwardly at an angle to the radial direction respecting said tube towards said tube, having length greater than distance by which said annular ring is spaced from said inner tube portion;
  iii. sleeve means between said ring and said tube;
  iv. said sleeve means having a second generally radial passageway therethrough defining orifices at respective outer and inner surfaces of said sleeve and receiving said finger means therein;
  v. said second generally radial passageway tapering from said outer surface of said sleeve to said inner surface of said sleeve to permit said finger means to remain relatively unflexed at a first position of said ring relative to said tube but causing said finger means to contact a wall portion of said second passageway and be deflected radially inwardly thereby to exit said second passageway at said inner orifice and intersectingly contact said tube to grippingly engage and immobilize said tube relative to said annular ring upon rotation of said annular ring relative to said tube.

4. The inversionary tube of claim 3 wherein said second passageway wall portion contacted by said finger means upon rotation of said annular ring relative to said tube is radial with respect to said tube.

5. The inversionary tube of claim 4 wherein said second passageway has a second wall portion, generally facing said wall portion which is radial with respect to said tube, said second wall portion being angularly disposed with respect to the radial and axial directions and being at substantially the angle of extension of said finger means from said annular ring in an unflexed condition.

6. An inversionary tube for use as a catheter and the like, comprising:
 a. a transversely flexible continuous tube of unitary construction having two ends, being doubled back onto itself at a connecting fold to define inner and outer tube portions in slideable contact with one another, said tube having a generally cylindrical transverse cross-section over the tube axial length;
 b. said inner tube portion slidably residing within said outer tube portion and being axially moveable into and out of said outer tube portion to change relative lengths of said outer and inner tube portions and position of said connecting fold;
 c. said tube end defining terminus of said inner tube portion remote from said connecting fold extending axially beyond said tube end defining terminus of said outer tube portion remote from said connecting fold so that said inner tube portion is longer than said outer tube portion;
 d. said tube having sufficient resistance to bending that axial force, applied to a part of said inner tube portion extending out of said outer tube portion, when applied in a direction towards said connecting fold is axially transmitted through said inner tube portion to said connecting fold and resolves into radially outward force, which when of sufficient magnitude, transforms said inner tube portion at said connecting fold into said outer tube portion thereby lengthening said outer tube portion and shortening said inner tube portion;
 e. indicia on inner and outer surfaces of said inversionary tube to indicate the length of said inversionary tube, said indicia being registered at twice the distance of the indicated length;
 f. a region of enlarged diameter proximate said end of inner tube portion to prevent said said end of inner tube portion from entering into and beyond said end of outer tube portion; wherein
  i. said tube is generally cylindrical;
  ii. said tube includes an internal channel which is generally cylindrical;
  iii. said tube has sufficient resistance to stretching that axial force, when applied to a part of said inner tube portion extending out of said outer tube portion away from said connecting fold, is axially transmitted by said inner tube portion to said connecting fold and resolves into radially inward force which, when of sufficient magnitude, transforms said outer tube portion at said connecting fold into said inner tube portion thereby shortening said outer tube portion and lengthening said inner tube portion;

iv. the enclosed surface defined by the interface of said inner tube portion and said outer tube portion has a lubricant as an integral part of said tube surface to facilitate movement of said inner tube portion relative to said outer tube portion;

v. said bonded lubrication coating is teflon;

vi. said inner tube portion is in sliding contact with said outer tube portion over the entire axial length of said outer tube portion overlapping said inner tube portion.

7. The inversionary tube of claim 6 wherein said cylindrical transverse cross-section is uniform over the tube axial length.

8. The inversionary tube of claim 7 wherein said tube wall thickness is uniform along the tube axial length.

9. An inversionary tube for use as a catheter and the like, comprising:

a. a transversely flexible continuous tube of unitary construction having two ends, being doubled back onto itself at a connecting fold to define inner and outer tube portions in slideable contact with one another, said tube having a generally cylindrical transverse cross-section over the tube axial length;

b. said inner tube portion slidably residing within said outer tube portion and being axially moveable into and out of said outer tube portion to change relative lengths of said outer and inner tube portions and position of said connecting fold;

c. said tube end defining terminus of said inner tube portion remote from said connecting fold extending axially beyond said tube end defining terminus of said outer tube portion remote from said connecting fold so that said inner tube portion is longer than said outer tube portion;

d. said tube having sufficient resistance to buckling that axial force, applied to a part of said inner tube portion extending out of said outer tube portion, when applied in a direction towards said connecting fold is axially transmitted through said inner tube portion to said connecting fold and resolves into radially outward force, which when of sufficient magnitude, transforms said inner tube portion at said connecting fold into said outer tube portion thereby lengthening said outer tube portion and shortening said inner tube portion;

e. a region of enlarged diameter proximate said end of inner tube portion to prevent said said end of inner tube portion from entering into and beyond said end of outer tube portion; wherein i. said tube includes an internal channel which is generally cylindrical;

ii. said tube has sufficient resistance to stretching that axial force, when applied to a part of said inner tube portion extending out of said outer tube portion away from said connecting fold, is axially transmitted by said inner tube portion to said connecting fold and resolves into radially inward force which, when of sufficient magnitude, transforms said outer tube portion at said connecting fold into said inner tube portion thereby shortening said outer tube portion and lengthening said inner tube portion;

iii. said inner tube portion is in sliding contact with said outer tube portion over the entire axial length of said outer tube portion overlapping said inner tube portion.

* * * * *